(12) United States Patent
Gailly et al.

(10) Patent No.: US 6,650,928 B1
(45) Date of Patent: Nov. 18, 2003

(54) COLOR PARAMETRIC AND COMPOSITE MAPS FOR CT PERFUSION

(75) Inventors: Jean-Loup Gailly, Rueil-Malmaison (FR); Robert Senzig, Germantown, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 69 days.

(21) Appl. No.: 09/723,128

(22) Filed: Nov. 27, 2000

(65) Prior Publication Data (65)

(51) Int. Cl.[7] .............. A61B 5/00; A61B 5/05; A61B 6/00

(52) U.S. Cl. .............. 600/425; 600/427; 600/431; 382/128; 128/922

(58) Field of Search .............. 600/425, 427, 600/431; 128/922; 382/128

(56) References Cited

U.S. PATENT DOCUMENTS

| | | | |
|---|---|---|---|
| 4,109,647 A | 8/1978 | Stern et al. | |
| 4,641,668 A | 2/1987 | Namekawa | |
| 4,862,894 A | 9/1989 | Fujii | |
| 5,377,681 A * | 1/1995 | Drane | 600/431 |
| 5,431,161 A * | 7/1995 | Ryals et al. | 128/653.1 |
| 5,438,989 A * | 8/1995 | Hochman et al. | 128/653.1 |
| 5,588,437 A | 12/1996 | Byrne et al. | |
| 5,699,799 A * | 12/1997 | Xu et al. | 324/306 |
| 5,797,396 A * | 8/1998 | Geiser et al. | 382/128 |
| 5,803,914 A * | 9/1998 | Ryals et al. | 600/407 |
| 5,873,829 A | 2/1999 | Kamiyama et al. | |
| 6,167,296 A * | 12/2000 | Shahidi | 600/427 |
| 6,241,672 B1 | 6/2001 | Hochman et al. | |
| 6,285,898 B1 * | 9/2001 | Ben-Haim | 600/374 |
| 2002/0065467 A1 * | 5/2002 | Schutt | 600/454 |

* cited by examiner

*Primary Examiner*—Joseph Pelham
(74) *Attorney, Agent, or Firm*—Carl B. Horton, Esq.; Armstrong Teasdale LLP

(57) ABSTRACT

The present invention is, in one embodiment, a method for facilitating the analysis of computed tomographic (CT) images. The method includes steps of: acquiring attenuation data of a patient using a CT imaging system; reconstructing images of the patient using the acquired attenuation data; mapping intensity data from at least one reconstructed image into a color image using a color mapping indicative of physiological thresholds; and displaying the color image.

Embodiments of the present invention facilitate the assessment of images and differences between images for functional image data and for perfusion-related imaging data.

28 Claims, 6 Drawing Sheets

COLOR PARAMETRIC AND COMPOSITE MAPS FOR CT PERFUSION

BACKGROUND OF THE INVENTION

This invention relates generally to methods and apparatus for facilitating computed tomographic (CT) image assessment, and more particularly to methods and apparatus for enhancing functional data on CT images.

In at least some computed tomography (CT) imaging system configurations, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. X-ray sources typically include x-ray tubes, which emit the x-ray beam at a focal spot. X-ray detectors typically include a collimator for collimating x-ray beams received at the detector, a scintillator adjacent the collimator, and photodetectors adjacent the scintillator.

Computed tomography (CT) is an anatomical imaging modality, but recently there have been advances that give some functional imaging capabilities to CT. For example, one known image software package for CT perfusion provides facilities for a user to process dynamic image data and to generate functional information and images that include functional image data relating to perfusion. The software uses changes in image intensity as a function of time to generate the information and the images. However, CT has classically been a grayscale-only modality, and it is difficult to assess differences in data on such images.

There exist known embodiments of other imaging modalities, such as nuclear medicine and positron emission tomography (PET), that regularly utilize functional maps to show differences. Color is often utilized with these modalities to give better discrimination than grayscale maps in the assessment of the displayed data.

CT Perfusion is a functional imaging software and is similar to perfusion packages in nuclear medicine or MR but is a unique use for CT.

It would therefore be desirable to provide methods and apparatus for computed tomographic imaging that facilitated the assessment of images, and differences between images, especially for functional image data, and more particularly for perfusion-related imaging data.

BRIEF SUMMARY OF THE INVENTION

One embodiment of the present invention is therefore a method for facilitating the analysis of computed tomographic (CT) images. The method includes steps of: acquiring attenuation data of a patient using a CT imaging system; reconstructing images of the patient using the acquired attenuation data; mapping intensity data from at least one reconstructed image into a color image using a color mapping indicative of physiological thresholds; and displaying the color image.

Embodiments of the present invention facilitate the assessment of images and differences between images for functional image data and for perfusion-related imaging data.

DETAILED DESCRIPTION OF THE INVENTION

Figure 1:
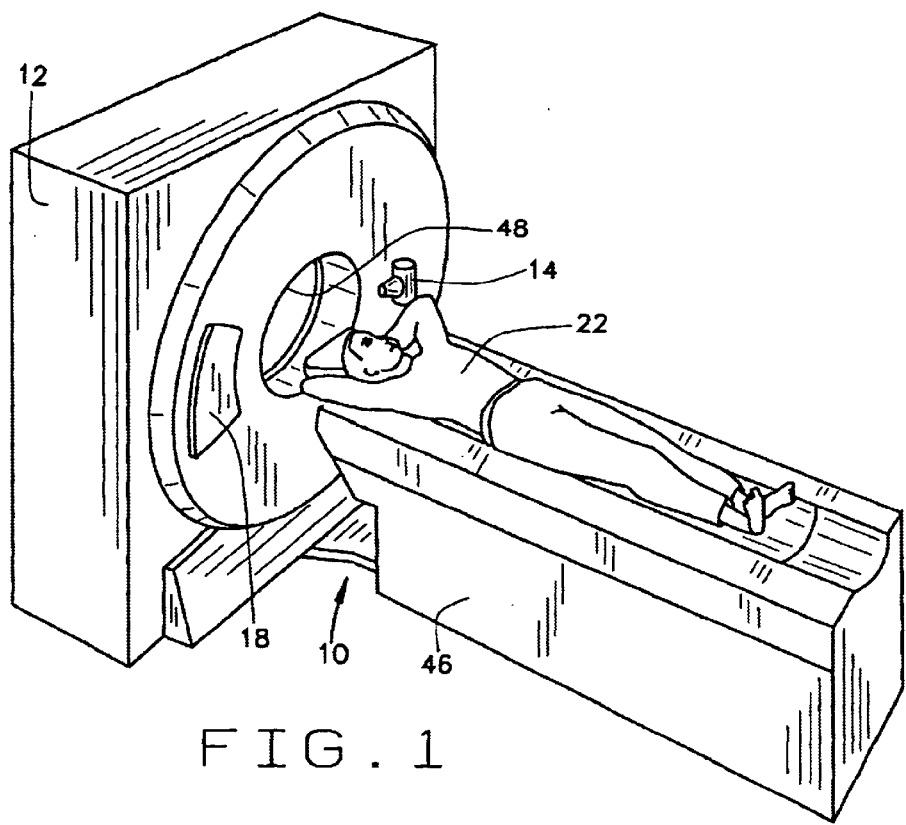
FIG. 1 is a pictorial view of a CT imaging system.
Figure 2:
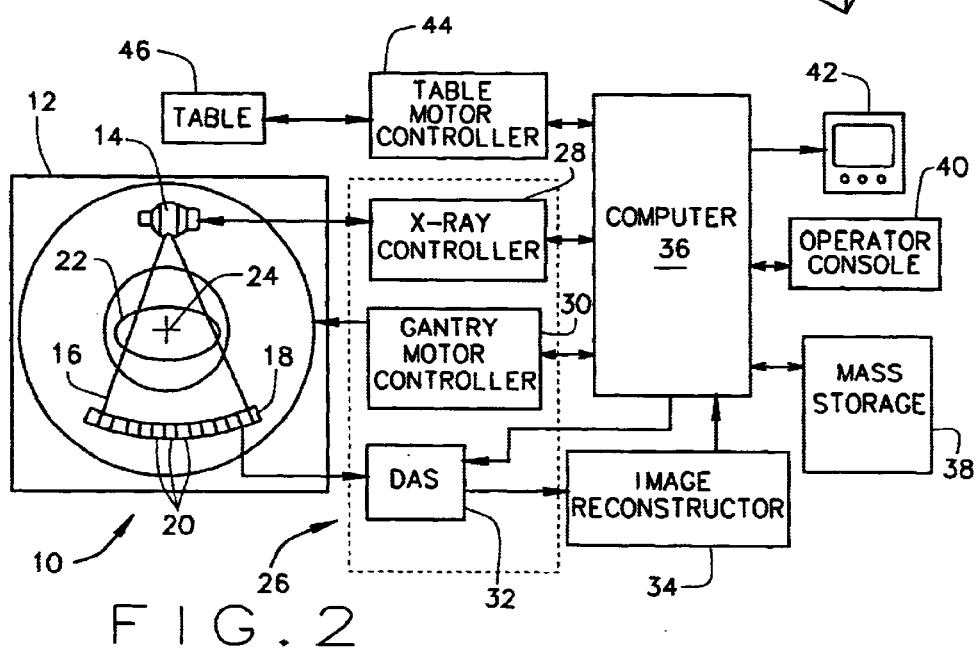
FIG. 2 is a block schematic diagram of the system illustrated in FIG. 1.

In one embodiment of the present invention, computed tomographic images are used. Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 which together sense the projected x-rays that pass through an object, such as a medical patient 22. Each detector element 20 produces an electrical signal that represents the intensity of an impinging x-ray beam and hence the attenuation of the beam as it passes through object or patient 22. During a scan to acquire x-ray projection data, gantry 12 and the components mounted thereon rotate about a center of rotation 24. In one embodiment, and as shown in FIG. 2, detector elements 20 are arranged in one row so that projection data corresponding to a single image slice is acquired during a scan. In another embodiment, detector elements 20 are arranged in a plurality of parallel rows, so that projection data corresponding to a plurality of parallel slices can be acquired simultaneously during a scan.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high speed image reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

Figure 3:
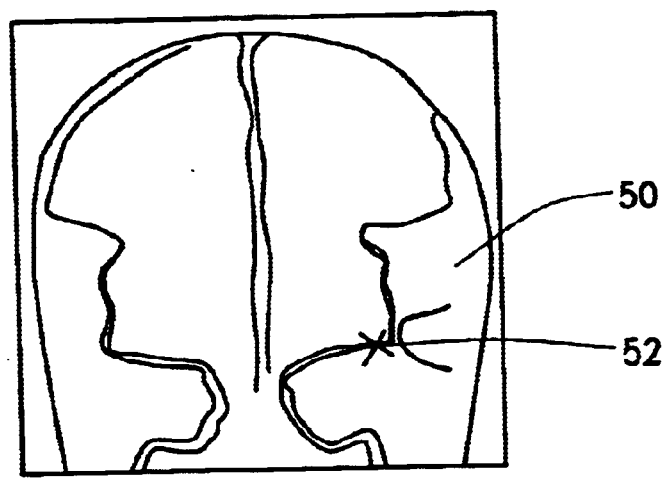
FIG. 3 is a representation of an anteroposterior projection of a head of a patient showing a potential location of a blockage.

In one embodiment and referring to FIG. 3, blood flow parameters of an organ of patient 22 such as brain 50 are measured by injecting a substance (for example, one containing iodine) into patient 22 that produces a contrasting appearance on CT images. For example, blood flow, blood volume, and mean transit time can be measured by examining the perfusion of the contrasting substance, which allows blockages 52 to be recognized. A blockage in one embodiment of the invention causes a change in color because of the change in volume, flow, or mean transit time.

In one embodiment of the present invention, maps with different color schemes are used for CT perfusion parametric images to facilitate their assessment. For example, display 42 is a color display, and software in computer 36 uses a mapping of intensities to color to enhance images for analysis. The software compares reconstructed images denoting the same region at different times, the software denote differences in measurements, as a function of time, of quantities such as blood flow, blood volume, and mean transit time for blood containing the injected substance to move through a cell. Depending upon the intended purpose of the images selected for display, intensities or intensity differences are mapped onto a set of colors by the software and the images are displayed on color display 42. One or more types of color maps are available for use in one embodiment. Examples of suitable maps include rainbow maps (i.e., maps in which a range of intensities or intensity differences are mapped into a range of colors having the same sequence as a rainbow spectrum), 3 colors, inverted rainbow, "Hot Iron" (in which colors range from yellow to red, with orange colors for intermediate intensities or intensity differences) and "Puh Thallium" (a color map in which the colors are somewhat darker than the rainbow colors). The two latter maps are similar to those used in conjunction with nuclear medicine imaging modality. In addition, colors representing intensities (or intensity differences) are mapped using threshold values that correspond to a physiological threshold. For example, to facilitate detection of tissues in which a stroke is occurring, blues are mapped to threshold levels selected to show where the stroke is occurring. On the other hand, greens are mapped to threshold areas of lower intensity in a reconstructed image representing healthy tissues, and red is mapped to areas having intensities characteristic of blood vessels. Such mappings are useful for assessment of blood flow.

Figure 4:
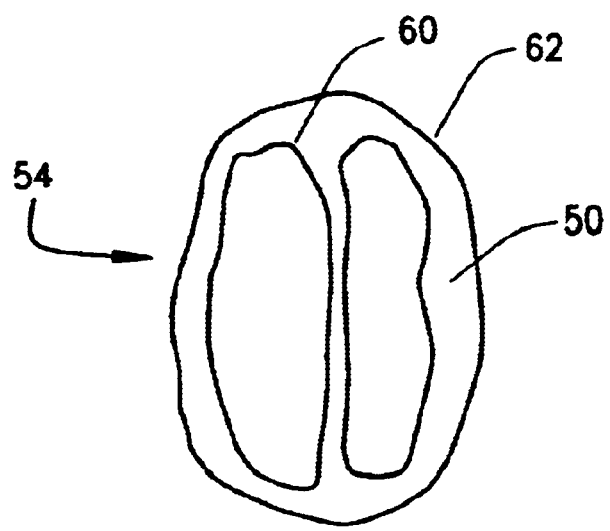
FIG. 4 is a representation of a CT anatomical image
Figure 5:
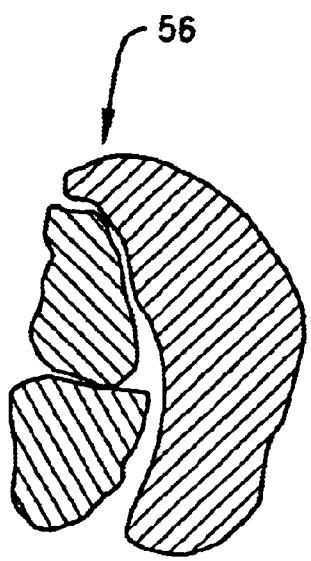
FIG. 5 is a representation of a CT parametric image.
Figure 6:
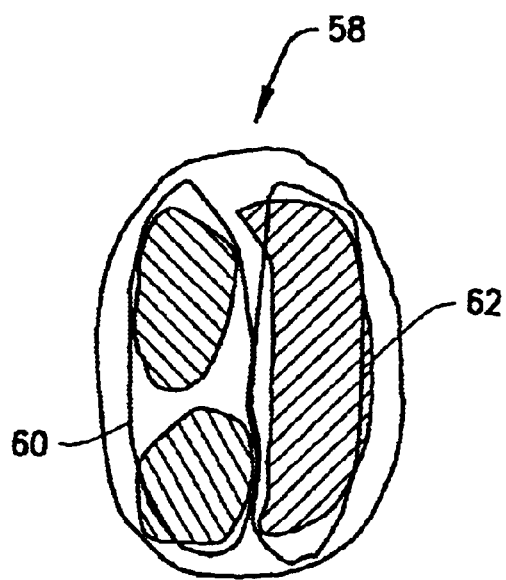
FIG. 6 is a representation of a CT parametric image overlaid over a CT anatomical image.

In one embodiment, parametric data for functional imaging is used in the display of color maps. Thus, intensities in the reconstructed image correspond to the parametric data. Also, and referring to FIGS. 4, 5, and 6 CT anatomical images 54 (images acquired beforehand, without injection of the perfusion substance) and parametric data images 56 (wherein each type of shading in FIG. 5 represents a different color in this example) are overlaid 58. Overlaid image 58 facilitates correlation of the parametric data 56 with the anatomy 54 of patient 22. For example, in one embodiment, the image data acquired beforehand is image data for brain structures 60, 62 of a patient, and a preprocessing and a post-processing image (i.e., one taken in the presence of perfusion) are overlaid. The opacity of the overlaid image 56 is made adjustable so that, in the case of overlaid parametric data, for example, more or less of the anatomical data can be seen beneath it, as desired. In one embodiment, maps for mean transit time for CT perfusion are used as the parametric data.

Figure 7:
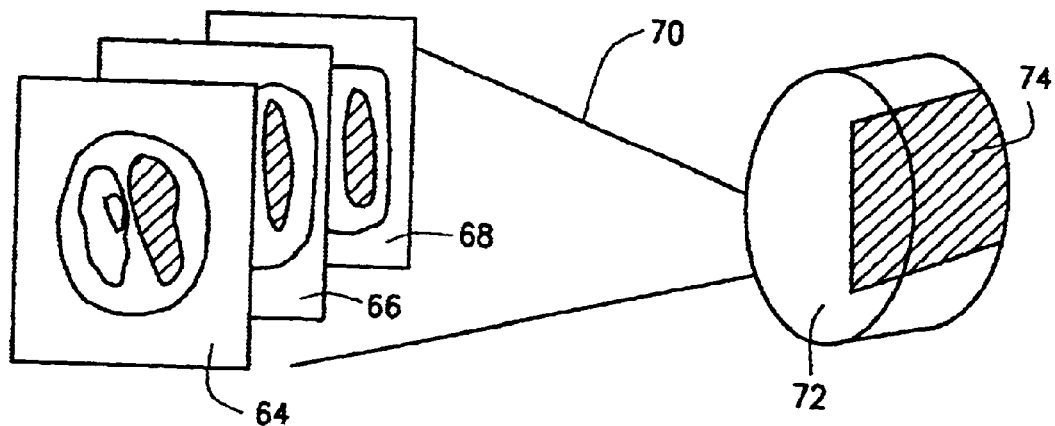
FIG. 7 is a representation of the combination of several composite images or slices into a 3D (three dimensional) image showing 3D functional data.

In another embodiment of the present invention and referring to FIG. 7, a plurality of composite images or slices 64, 66, 68 are combined 70 to produce a 3D image 72 (i.e., a perspective image) showing 3D functional data 74 in color.

In one embodiment of the present invention, a rainbow color map emphasizes ischemia areas (i.e., areas with a lower blood volume) as cold-colored areas. In another embodiment, a three-color color map allows a visual segmentation of damaged, healthy, and hyper-vascularized tissue. In yet another embodiment, an inverse rainbow color map emphasizes areas with longer transit time as cold-colored areas. These areas are surrogates of an ischemic process.

Figure 8:
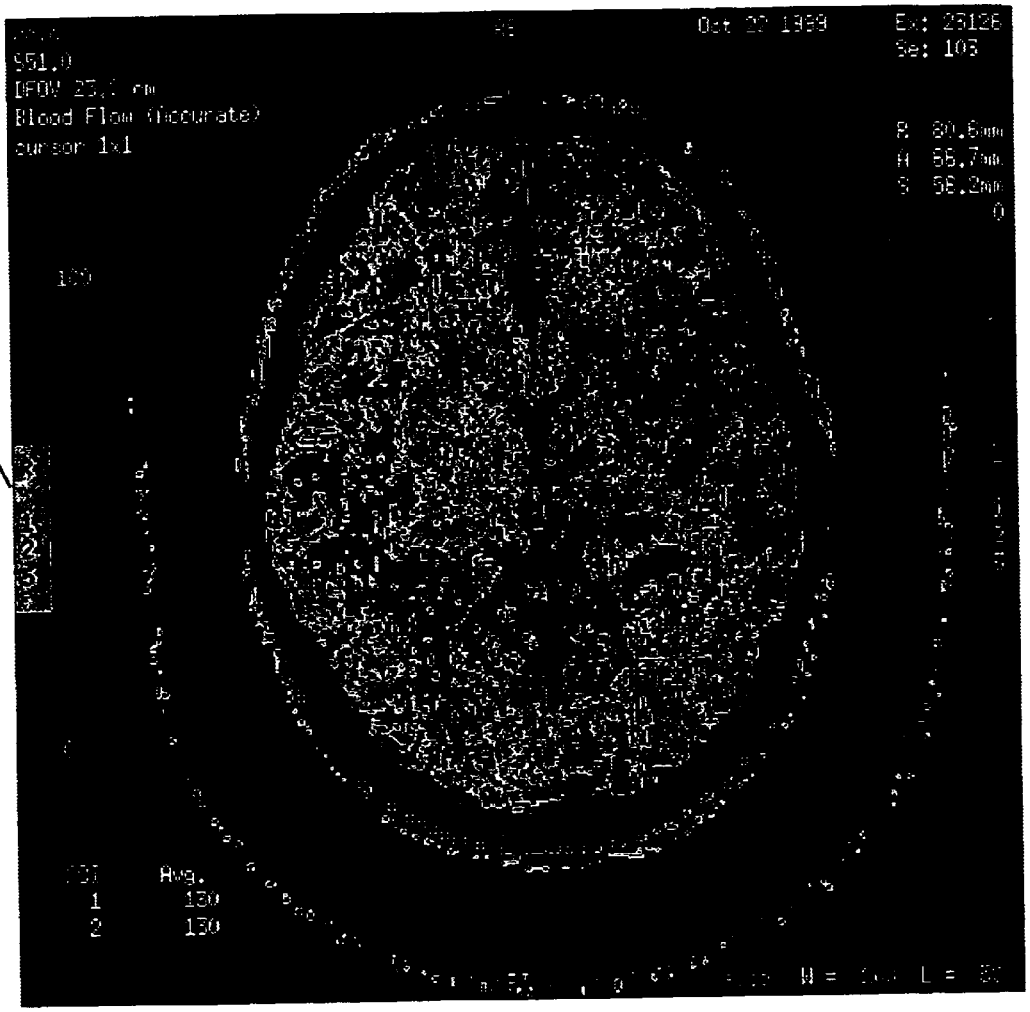
FIG. 8 is a sample three-color parametric image.
Figure 9:
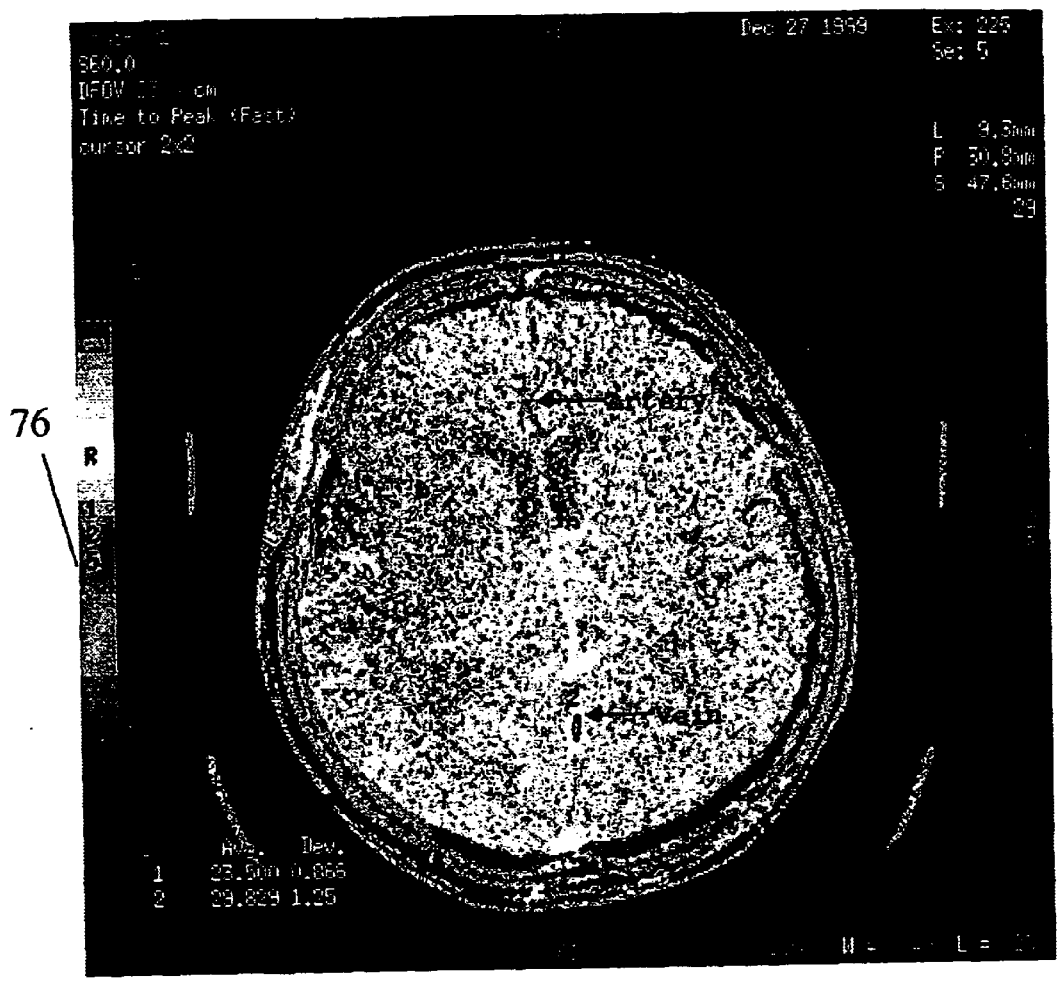
FIG. 9 is a sample rainbow colored composite image.
Figure 8:
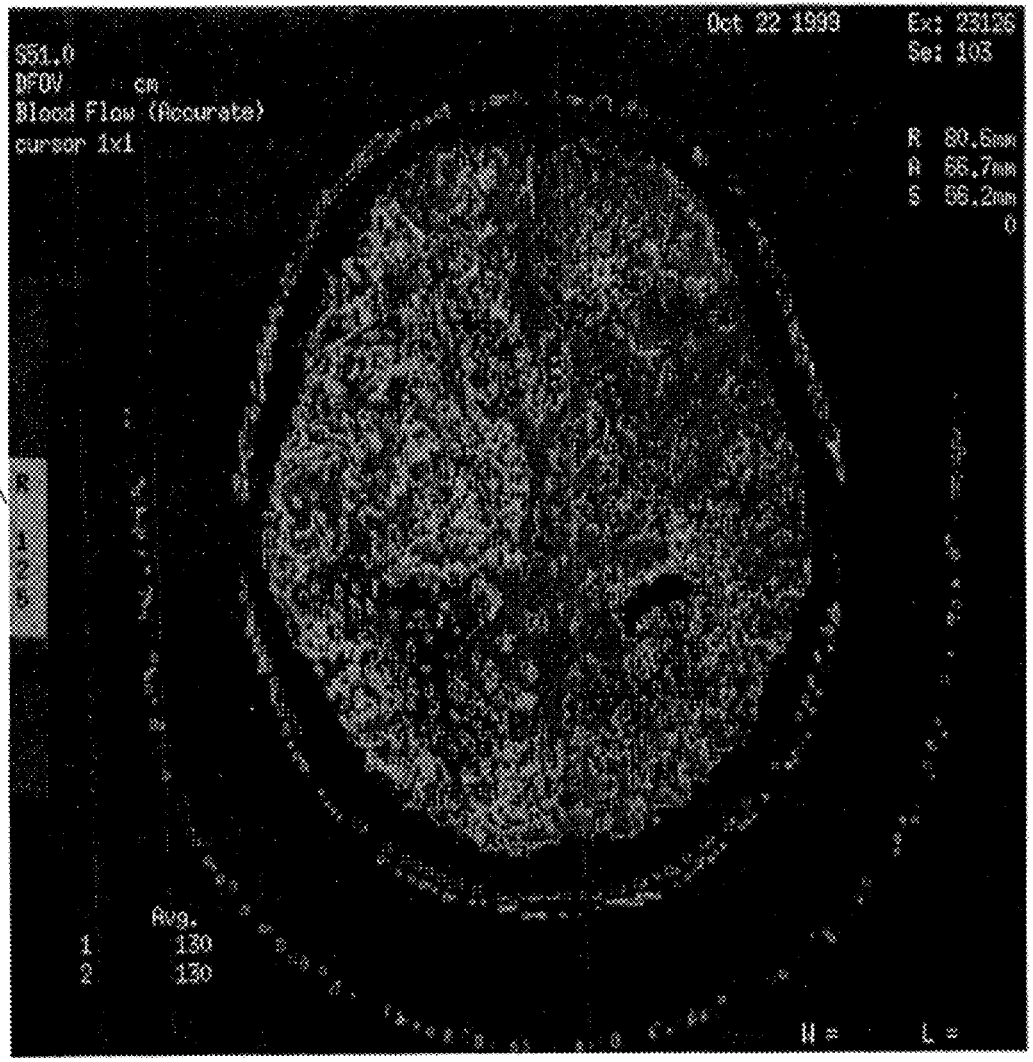
Figure 9:
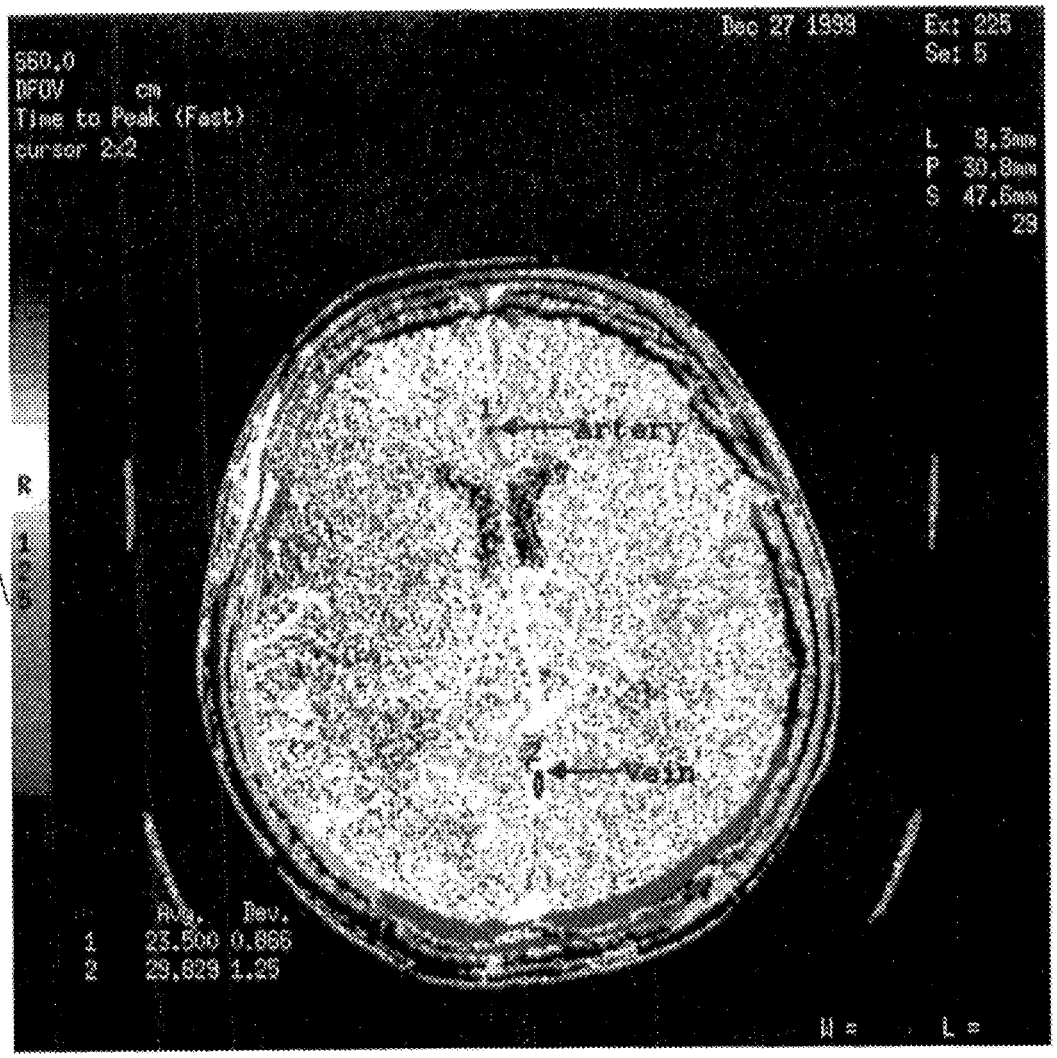

FIG. 8 is a sample three-color parametric image. FIG. 9 is a sample rainbow colored composite image. In each image, a mapping 76 of intensities or intensity differences to colors is shown.

These sample results show the results of a mapping of intensities of embodiments of the present invention and how such embodiments facilitate the assessment of images, and differences between images, for functional image data and for perfusion-related imaging data.

While the invention has been described in terms of various specific embodiments, those skilled in the art will recognize that the invention can be practiced with modification within the spirit and scope of the claims.

What is claimed is:

1. A method for facilitating the analysis of computed tomographic (CT) images, comprising:
   acquiring attenuation data including CT perfusion functional data of a patient using a CT imaging system;
   reconstructing images of the patient using the acquired attenuation data;
   mapping intensity data from at least one reconstructed image into a color CT perfusion parametric image using a color mapping indicative of physiological thresholds, wherein said mapping uses at least one of a rainbow color mapping, a three color mapping, a "Hot Iron" color mapping, and a "Puh Thallium" mapping; and
   displaying the color CT perfusion parametric image.

2. A method in accordance with claim 1 wherein said step of displaying a color CT perfusion parametric image comprises the step of displaying differences in measurements of a member of the group consisting of blood flow, blood volume, and mean transit time for movement of blood.

3. A method in accordance with claim 1 wherein said mapping uses a rainbow color mapping.

4. A method in accordance with claim 1 wherein said mapping uses a three color mapping.

5. A method in accordance with claim 1 wherein said mapping uses a "Hot Iron" color mapping.

6. A method in accordance with claim 1 wherein said mapping uses a "Puh Thallium" color mapping.

7. A method in accordance with claim 1 wherein said step of displaying a color CT perfusion parametric image comprises the step of overlaying two CT images.

8. A method in accordance with claim 7 wherein said step of overlaying two CT image comprises the step of overlaying an image representative of parametric data over an anatomical image.

9. A method in accordance with claim 8 further comprising the step of adjusting opacity of the overlaid image.

10. A method in accordance with claim 1 wherein said mapping uses a rainbow color mapping indicative of ischemia areas.

11. A method in accordance with claim 1 wherein said mapping uses a three-color color map indicative of damaged, healthy, and hyper-vascularized tissue.

12. A method in accordance with claim 3 wherein said mapping uses an inverse rainbow color map emphasizing areas with longer transit times.

13. A computed tomographic (CT) imaging system comprising a color display, a rotating gantry, a radiation source on the rotating gantry, and a detector array opposite the radiation source on the rotating gantry, said detector array configured to acquire attenuation data including CT perfusion functional data from radiation emitted by said radiation source and passing through a patient between said radiation source and said detector array, said CT imaging system configure to:
reconstruct images of the patient using said acquired attenuation data;
map intensity data from at least one said reconstructed image into a color CT perfusion parametric image using a color mapping indicative of physiological thresholds, wherein said mapping uses at leasts one of a rainbow color mapping, a three color mapping, a "Hot Iron" color mapping, and a "Puh Thallium" mapping; and
display the color CT perfusion parametric image on said color display.

14. A CT imaging system in accordance with claim 13 wherein to display said color CT perfusion parametric image, said imaging system is configured to display differences in measurements of a member of the group consisting of blood flow, blood volume, and mean transit time for movement of blood.

15. A CT imaging system in accordance with claim 13 configured to map intensity data using a rainbow color mapping.

16. A CT imaging system in accordance with claim 13 configured to map intensity data using a three color mapping.

17. A CT imaging system in accordance with claim 13 configured to map intensity data using a "Hot Iron" color mapping.

18. A CT imaging system in accordance with claim 13 configured to map intensity data using a "Puh Thallium" color mapping.

19. A CT imaging system in accordance with claim 13 wherein to display a color CT perfusion parametric image, said CT imaging system is configured to overlay two CT images.

20. A CT imaging system in accordance with claim 19 wherein to overlay two CT images, said CT imaging system is configured to overlay an image representative of parametric data over an anatomical image.

21. A CT imaging system in accordance with claim 20 further configured to adjust opacity of the overlaid image.

22. A CT imaging system in accordance with claim 13 configured to utilize a rainbow color mapping indicative of ischemia areas.

23. A method in accordance with claim 13 configured to utilize a three-color color map indicative of damaged, healthy, and hyper-vascularized tissue.

24. A method in accordance with claim 13 configured to utilize an inverse rainbow color map emphasizing areas with longer transit times.

25. A method for facilitating the analysis of computed tomographic (CT) images, comprising the steps of:
acquiring attenuation data including CT perfusion functional data of a patient using a CT imaging system;
reconstructing a plurality of images of the patient using the acquired attenuation data;
mapping intensity data from the plurality of reconstructed images into a plurality of color CT perfusion parametric images using a color mapping indicative of physiological thresholds, a "Hot Iron" color mapping, and a "Puh Thallium" mapping; and
combining the plurality of color CT perfusion parametric images to produce a 3D image showing 3D CT perfusion functional data in color.

26. A method in accordance with claim 25 wherein the 3D image is a perspective image.

27. A computed tomographic (CT) imaging system comprising a color display, a rotating gantry, a radiation source on the rotating gantry, and a detector array opposite the radiation source on the rotating gantry, said detector array configured to acquire attenuation data including CT perfusion functional data from radiation emitted by said radiation source and passing through a patient between said radiation source and said detector array, said CT imaging system configured to:
reconstruct a plurality of images of the patient using said acquired attenuation data including CT perfusion functional data;
map intensity data from said plurality of reconstructed images into a plurality of color CT perfusion parametric images using a color mapping indicative of physiological thresholds, wherein said mapping uses at least one of a rainbow color mapping, a three color mapping, a "Hot Iron" color mapping, and a "Puh Thallium" mapping;
combine the plurality of color CT perfusion parametric images to produce a 3D image showing 3D CT perfusion functional data in color; and
display said 3D image on said color display.

28. A CT imaging system in accordance with claim 27 wherein said 3D image is a perspective image.

* * * * *

UNITED STATES PATENT AND TRADEMARK OFFICE
CERTIFICATE OF CORRECTION

PATENT NO. : 6,650,928 B1
DATED : November 18, 2003
INVENTOR(S) : Gailly et al.

It is certified that error appears in the above-identified patent and that said Letters Patent is hereby corrected as shown below:

Column 4,
Line 65, delete "two CT image" and insert -- two CT images --.

Column 5,
Line 9, delete "3 wherein" and insert -- 1 wherein --.
Line 20, delete "configure to" and insert -- configured to --.
Line 26, delete "at leasts one" and insert -- at least one --.

Column 6,
Line 21, after "thresholds," insert -- wherein said mapping uses at least one of a rainbow color mapping, a three color mapping, --.

Signed and Sealed this

Third Day of January, 2006

JON W. DUDAS
*Director of the United States Patent and Trademark Office*

UNITED STATES PATENT AND TRADEMARK OFFICE
CERTIFICATE OF CORRECTION

PATENT NO.        : 6,650,928 B1                                              Page 1 of 3
APPLICATION NO. : 09/723128
DATED             : November 18, 2003
INVENTOR(S)       : Gailly et al.

It is certified that error appears in the above-identified patent and that said Letters Patent is hereby corrected as shown below:

After the "Brief Description of Drawings", column 2, line 8, before the line beginning "FIG. 1 is a", insert the paragraph -- The file of this patent contains at least one drawing executed in color. Copies of this patent with color drawings will be provided by the Patent and Trademark Office upon request and payment of the necessary fees. --.

Signed and Sealed this

Thirtieth Day of September, 2008

JON W. DUDAS
*Director of the United States Patent and Trademark Office*

UNITED STATES PATENT AND TRADEMARK OFFICE
CERTIFICATE OF CORRECTION

PATENT NO. : 6,650,928 B1
APPLICATION NO. : 09/723128
DATED : November 18, 2003
INVENTOR(S) : Gailly et al.

Page 2 of 3

It is certified that error appears in the above-identified patent and that said Letters Patent is hereby corrected as shown below:

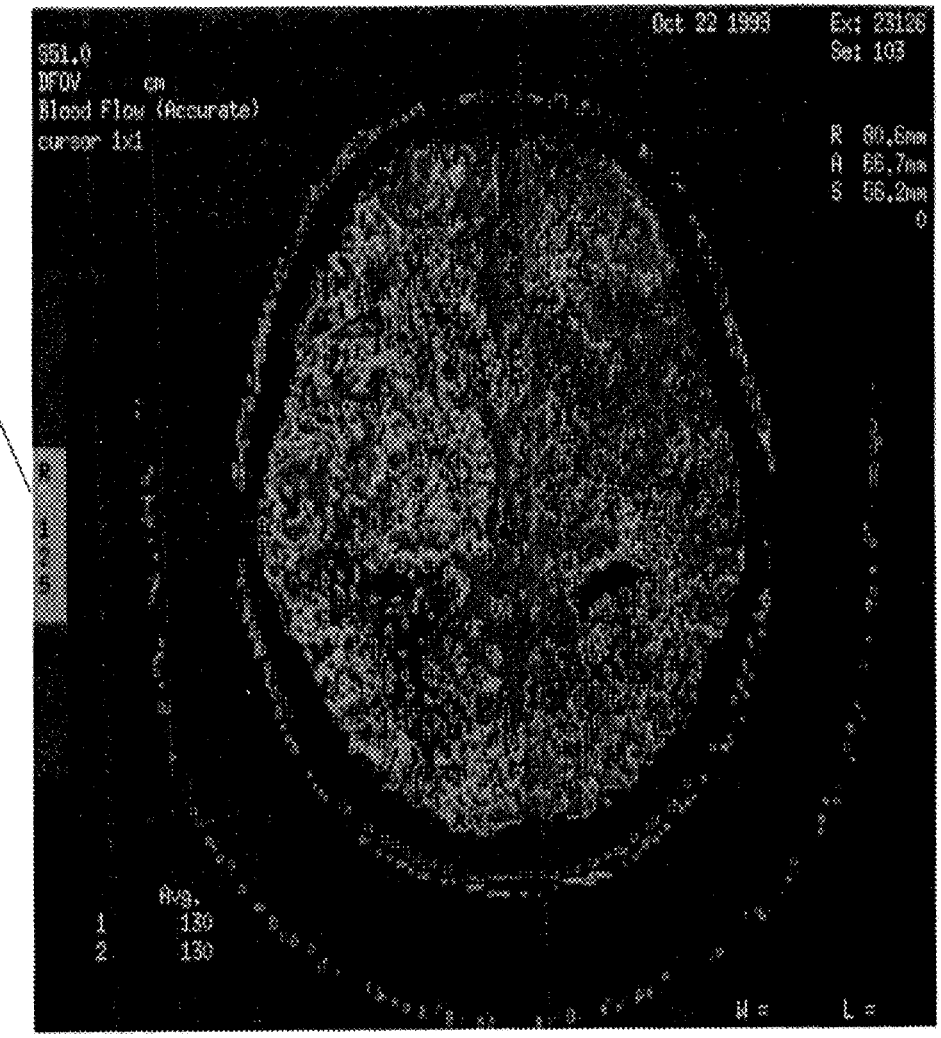

*Fig. 8*

UNITED STATES PATENT AND TRADEMARK OFFICE
CERTIFICATE OF CORRECTION

PATENT NO. : 6,650,928 B1
APPLICATION NO. : 09/723128
DATED : November 18, 2003
INVENTOR(S) : Gailly et al.

It is certified that error appears in the above-identified patent and that said Letters Patent is hereby corrected as shown below:

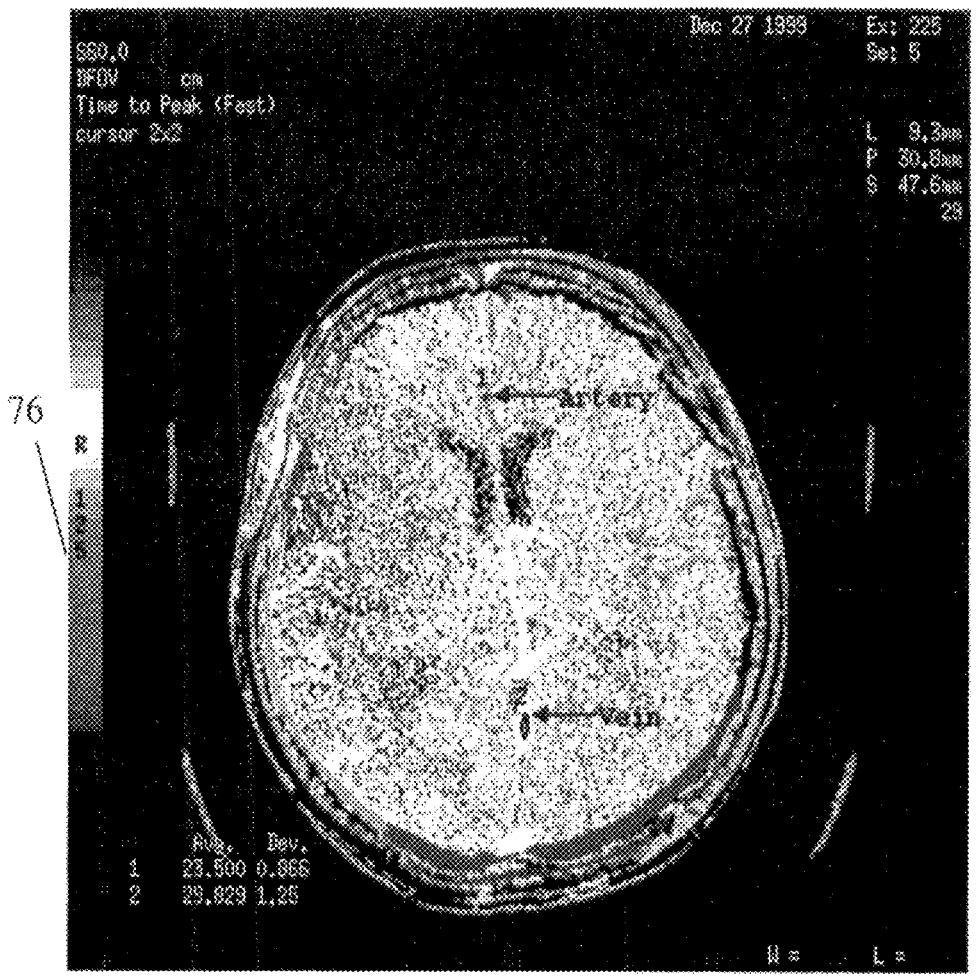

Fig. 9

UNITED STATES PATENT AND TRADEMARK OFFICE
CERTIFICATE OF CORRECTION

| | | |
|---|---|---|
| PATENT NO. | : 6,650,928 B1 | |
| APPLICATION NO. | : 09/723128 | |
| DATED | : November 18, 2003 | |
| INVENTOR(S) | : Gailly et al. | |

It is certified that error appears in the above-identified patent and that said Letters Patent is hereby corrected as shown below:

Delete Drawing sheets 1-2, and substitute therefor the Drawing sheets, consisting of figs. 8-9 as shown on the attached pages.

After the "Brief Description of Drawings", column 2, line 8, before the line beginning "FIG. 1 is a", insert the paragraph -- The file of this patent contains at least one drawing executed in color. --

Signed and Sealed this

Seventh Day of October, 2008

JON W. DUDAS
*Director of the United States Patent and Trademark Office*